(12) United States Patent
Ueno et al.

(10) Patent No.: US 7,768,651 B2
(45) Date of Patent: Aug. 3, 2010

(54) OPTICAL COHERENCE TOMOGRAPHY APPARATUS BASED ON SPECTRAL INTERFERENCE AND AN OPHTHALMIC APPARATUS

(75) Inventors: Tokio Ueno, Nagoya (JP); Masaaki Hanebuchi, Nukata-gun (JP)

(73) Assignee: Nidek Co., Ltd., Gamagori-Shi (JP)

( * ) Notice: Subject to any disclaimer, the term of this patent is extended or adjusted under 35 U.S.C. 154(b) by 81 days.

(21) Appl. No.: 11/236,832

(22) Filed: Sep. 28, 2005

(65) Prior Publication Data

US 2006/0066869 A1 Mar. 30, 2006

(30) Foreign Application Priority Data

Sep. 30, 2004 (JP) ............................. 2004-289077

(51) Int. Cl.
*G01B 11/02* (2006.01)
(52) U.S. Cl. ..................................... 356/497
(58) Field of Classification Search ................ 356/497, 356/479, 488, 494, 499, 511, 455
See application file for complete search history.

(56) References Cited

U.S. PATENT DOCUMENTS

| | | | | |
|---|---|---|---|---|
| 5,565,986 A | * | 10/1996 | Knuttel | 356/456 |
| 5,579,112 A | * | 11/1996 | Sugiyama et al. | 356/479 |
| 5,956,141 A | * | 9/1999 | Hayashi | 356/496 |
| 6,377,349 B1 | | 4/2002 | Fercher | |
| 6,788,421 B2 | * | 9/2004 | Fercher et al. | 356/497 |
| 6,882,433 B2 | * | 4/2005 | Marron et al. | 356/512 |
| 7,061,625 B1 | * | 6/2006 | Hwang et al. | 356/511 |
| 2004/0201850 A1 | * | 10/2004 | Hajian et al. | 356/451 |
| 2005/0190371 A1 | * | 9/2005 | Knuttel | 356/479 |

FOREIGN PATENT DOCUMENTS

| | | |
|---|---|---|
| JP | A 11-325849 | 11/1999 |
| JP | A 2004-028970 | 1/2004 |

OTHER PUBLICATIONS

Frank Pedrotti and Leno Pedrotti, Introduction to Optics, Prentice-Hall Inc., Second Edition, 50-55.*
Frank Pedrotti and Leno Pedrotti, Introduction to Optics, Nov. 1992, Prentice-Hall Inc, Second Edition, p. 50-55.*

* cited by examiner

*Primary Examiner*—Tarifur Chowdhury
*Assistant Examiner*—Jonathan M Hansen
(74) *Attorney, Agent, or Firm*—Oliff & Berridge, PLC

(57) ABSTRACT

An optical coherence tomography apparatus based on spectral interference where object information can be speedily obtained and an information acquisition range in a depth direction can be enlarged, and an ophthalmic apparatus. The apparatus includes a first optical system for projecting light with short coherence length onto an object to form object light which is reflection light from the object, a second optical system for projecting light with short coherence length onto a reference surface to form reference light which is reflection light from the surface, an optical system for synthesizing the object light and the reference light to be interference light, dispersing the interference light into predetermined frequency components and photo-receiving the dispersed light with a photodetector, a device varying a spectral characteristic when the interference light is dispersed by the interference/dispersion/photo-receiving optical system, and a calculation part obtaining the information based on an output signal from the photodetector.

3 Claims, 3 Drawing Sheets

OPTICAL COHERENCE TOMOGRAPHY APPARATUS BASED ON SPECTRAL INTERFERENCE AND AN OPHTHALMIC APPARATUS

BACKGROUND OF THE INVENTION

1. Field of the Invention

The present invention relates to an apparatus for obtaining object information using optical coherence tomography (OCT) based on spectral interference, and specifically, relates to an ophthalmic apparatus for obtaining ocular information.

2. Description of Related Art

Conventionally, there is known an apparatus for obtaining object information including a sectional image, a surface shape and a depth dimension of an object using optical coherence tomography (OCT) based on spectral interference. This kind of apparatus, which does not drive a reference mirror, can obtain the object information more speedily than a normal apparatus using optical coherence tomography (OCT) not based on spectral interference.

However, the OCT apparatus based on spectral interference covers a narrower information acquisition range in a depth direction than the OCT apparatus not based on spectral interference. Though the information acquisition range in the depth direction can be enlarged by driving the reference mirror (see U.S. Pat. No. 6,377,349 B1, DE 19814057 A1, and Japanese Patent Application Unexamined Publication No. Hei11-325849), the object information cannot be speedily obtained on the contrary.

SUMMARY OF THE INVENTION

An object of the invention is to overcome the problems described above and to provide an optical coherence tomography (OCT) apparatus based on spectral interference where object information can be speedily obtained and an information acquisition range in a depth direction can be enlarged, and an ophthalmic apparatus.

To achieve the objects and in accordance with the purpose of the present invention, an apparatus for obtaining object information by optical coherent tomography based on spectral interference has a first projecting optical system for projecting light with short coherence length onto an object to form object light which is reflection light from the object, a second projecting optical system for projecting light with short coherence length onto a reference surface to form reference light which is reflection light from the reference surface, an interference/dispersion/photo-receiving optical system for synthesizing the object light and the reference light to be interference light, dispersing the interference light into predetermined frequency components and photo-receiving the dispersed light with a photodetector, spectral characteristic varying means for varying a spectral characteristic when the interference light is dispersed by the interference/dispersion/photo-receiving optical system, and a calculation part which obtains the object information based on an output signal from the photodetector.

Additional objects and advantages of the invention are set forth in the description which follows, are obvious from the description, or may be learned by practicing the invention. The objects and advantages of the invention may be realized and attained by the apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
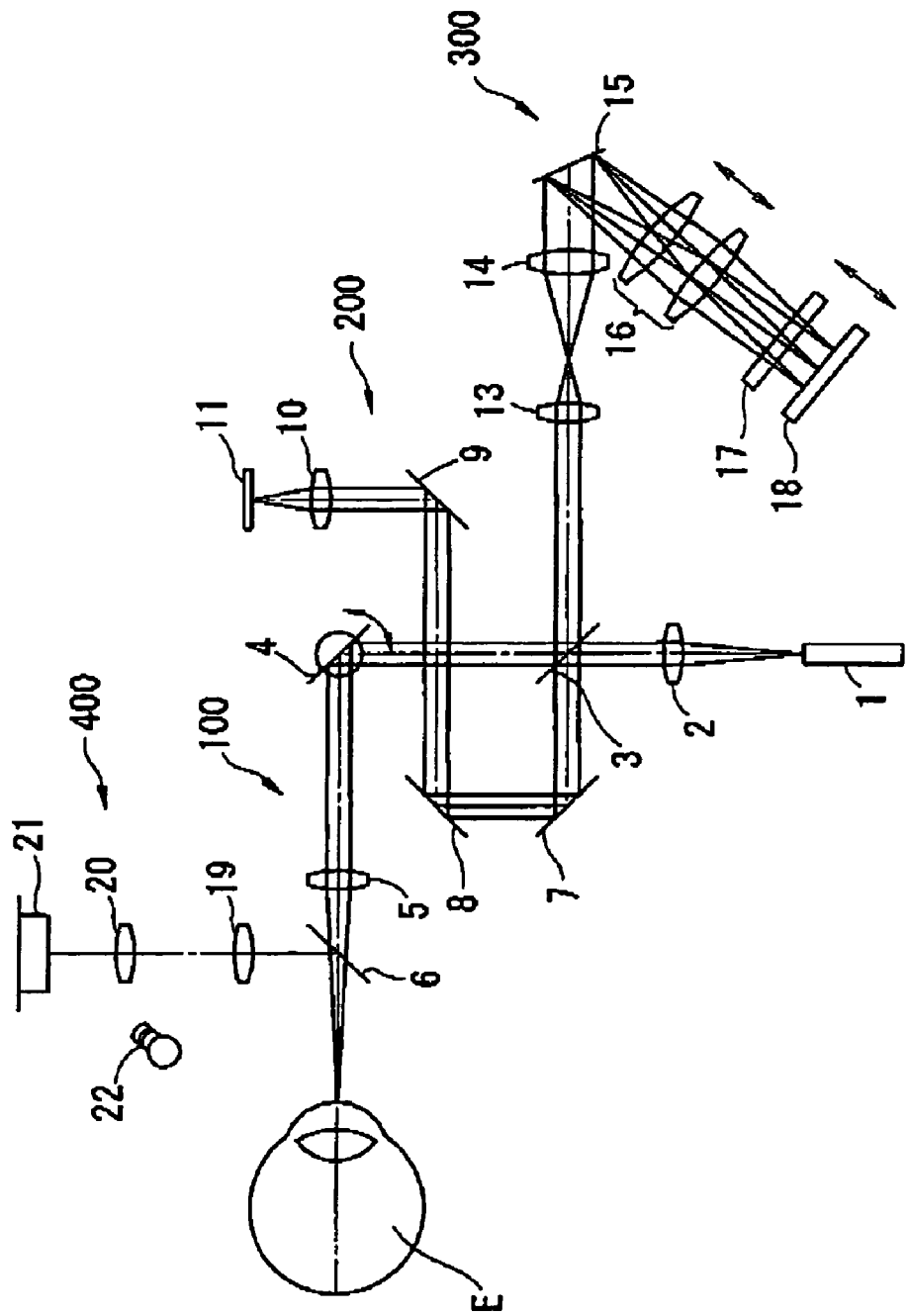
FIG. 1 is a view showing a schematic configuration of an optical system of an ophthalmic OCT apparatus based on spectral interference consistent with one preferred embodiment of the present invention.

A detailed description of one preferred embodiment of an optical coherence tomography (OCT) apparatus based on spectral interference and an ophthalmic apparatus embodied by the present invention is provided below with reference to the accompanying drawings. FIG. 1 is a view showing a schematic configuration of an optical system of an ophthalmic OCT apparatus based on spectral interference consistent with the preferred embodiment of the present invention. It should be noted that the apparatus consistent with the preferred embodiment is an apparatus for picking up a sectional image of an anterior segment of an eye which is an object, and its optical system includes an object-light projecting optical system, a reference-light projecting optical system, an interference/dispersion/photo-receiving optical system (an interference-signal detecting optical system), and an observation optical system. Though the apparatus consistent with the preferred embodiment includes also an alignment optical system for aligning the apparatus with the eye to have a predetermined positional relationship, a description thereof is omitted since an optical system similar to a known alignment optical system used in an objective eye refractive power measurement apparatus and the like may be employed.

<Object-Light Projecting Optical System>

An object-light projecting optical system 100 includes a light source 1, a collimator lens 2, a half mirror 3, a galvano mirror 4, an objective lens 5, and a dichroic mirror 6 which transmits near infrared light and reflects infrared light. The light source 1 such as a super luminescent diode (SLD) emits near infrared light with short coherence length. The light emitted from the light source 1 is made into parallel light by the collimator lens 2, and a part thereof passes through the half mirror 3. The light having passed through the half mirror 3 is reflected by the galvano mirror 4 and passes through the objective lens 5 and the dichroic mirror 6 to converge in the vicinity of a corneal vertex of an eye E. The galvano mirror 4 is rotated (oscillated) in a predetermined direction (in the preferred embodiment, a direction for scanning the light in an up/down direction with respect to the eye E). In addition, the galvano mirror 4 of which a reflection surface is positioned at a posterior focal point of the objective lens 5 is arranged in such a manner that an optical path length does not change.

<Reference-Light Projecting Optical System>

A reference-light projecting optical system 200 includes the light source 1, the collimator lens 2, the half mirror 3 which are shared with the object-light projecting optical system 100, total reflection mirrors 7 to 9, a condenser lens 10, and a reference mirror 11. The light from the light source 1 reflected by the half mirror 3 is reflected by the mirrors 7 to 9 and passes through the condenser lens 10 to converge at a reflection surface of the reference mirror 11.

<Interference/Dispersion/Photo-Receiving Optical System>

An interference/dispersion/photo-receiving optical system 300 includes an optical system for photo-receiving light reflected from the eye E (hereinafter also referred to as object light) and an optical system for photo-receiving light reflected by the reference mirror 11 (hereinafter also referred to as reference light).

The object-light photo-receiving optical system includes the dichroic mirror 6, the objective lens 5, the galvano mirror 4, the half mirror 3 which are shared with the object-light projecting optical system 100, a condenser lens 13, an expander lens 14, a grating mirror (diffraction grid) 15, a variable power lens group 16, a cylindrical lens 17, and a photodetector 18 having sensitivity to a near infrared range. The grating mirror 15 is arranged in such a manner that its reflection surface is positioned at an anterior focal point of the variable power lens group 16. In addition, the photodetector 18 is arranged in such a manner that its photo-receiving surface is positioned at a posterior focal point of the variable power lens group 16.

Reflection light brought by the light which is made to converge in the vicinity of the corneal vertex of the eye E by the object-light projecting optical system 100 (i.e., the object light) passes through the dichroic mirror 6 and the objective lens 5 and is reflected by the galvano mirror 4, and a part thereof is reflected by the half mirror 3. The light reflected by the half mirror 3 passes through the condenser lens 13 to once converge, passes through the expander lens 14 to have its light bundle diameter enlarged, and enters the grating mirror 15 to be dispersed into frequency components. The light dispersed by the grating mirror 15 passes through the variable power lens group 16 and the cylindrical lens 17 to converge at the photo-receiving surface of the photodetector 18. Incidentally, the light bundle diameter after the passage through the expander lens 14, grid intervals of the grating mirror 15, the variable power lens group 16, and the photodetector 18 are optimized in consideration of an information acquisition range in a depth direction of the eye E (a direction of an optical axis) and a resolution thereof. In addition, the variable power lens group 16 can be switched between at least two focal lengths, and thereby a spectral characteristic of the light to be dispersed can be varied.

The reference-light photo-receiving optical system includes the reference mirror 11, the condenser lens 10, the mirrors 9 to 7 and the half mirror 3 which are shared with the reference-light projecting optical system 200, and the condenser lens 13, the expander lens 14, the grating mirror 15, the variable power lens group 16, the cylindrical lens 17 and the photodetector 18 which are shared with the object-light photo-receiving optical system.

Reflection light brought by the light which is made to converge at the reflection surface of the reference mirror 11 by the reference-light projecting optical system 200 (i.e., the reference light) passes through the condenser lens 10 and is reflected by the mirrors 9 to 7, and a part thereof passes through the half mirror 3 to be synthesized with the object light. The reference light synthesized with the object light passes through the condenser lens 13 and the expander lens 14 to be dispersed into frequency components by the grating mirror 15, and passes through the variable power lens group 16 and the cylindrical lens 17 to converge at the photo-receiving surface of the photodetector 18. In this manner, the grating mirror 15, the variable power lens group 16, the cylindrical lens 17, and the photodetector 18 form a spectrometer part. Incidentally, the photodetector 18 is arranged in such a manner that its photo-receiving surface has a positional relationship conjugate with a cornea of the eye E. In addition, the cylindrical lens 17 acts to enlarge the light bundle diameter in a width direction of the photodetector 18, allowing the light to be photo-received on the photo-receiving surface of the photodetector 18 regardless of its placement error.

<Observation Optical System>

An observation optical system 400 includes the dichroic mirror 6, an objective lens 19, an image-forming lens 20, and an image-pickup element 21 having sensitivity to an infrared range. The image-pickup element 21 is arranged in such a manner that its image-pickup surface has a positional relationship conjugate with a pupil of the eye E. A light source 22 such as a light emitting diode (LED) emits infrared light and illuminates an anterior segment of the eye E. A front image of the anterior segment illuminated by the light source 22 is picked up by the image-pickup element 21 and displayed on a monitor 41.

Figure 2:
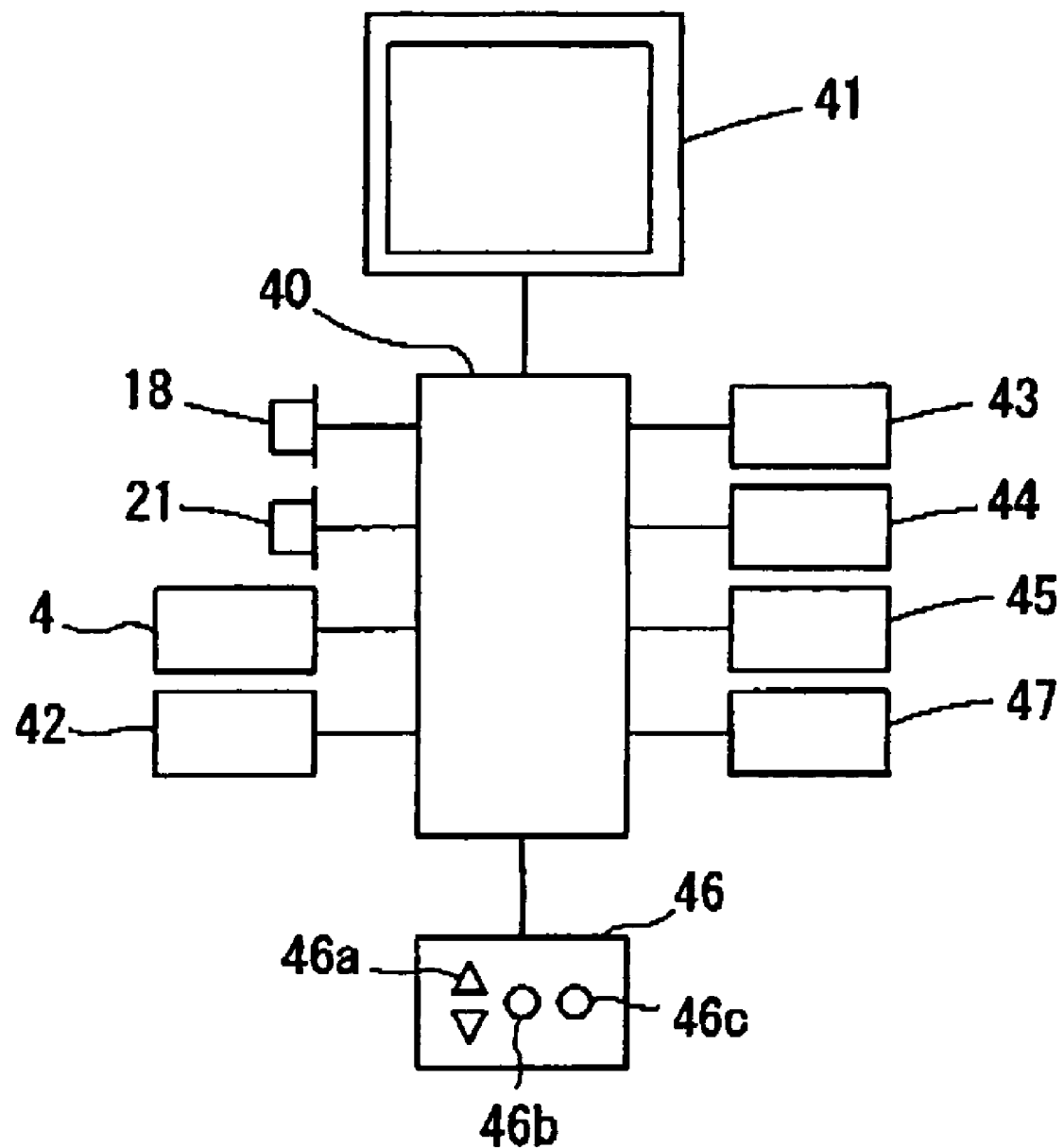
FIG. 2 is a schematic block diagram of a control system of the ophthalmic OCT apparatus.

FIG. 2 is a schematic block diagram of a control system of the ophthalmic OCT apparatus. A control part 40 performs control of the entire apparatus, and the like. The control part 40 is connected with the galvano mirror 4, the photodetector 18, the image-pickup element 21, the monitor 41, a calculation/processing part 42, driving parts (units) 43 to 45, a controller 46, a storage part 47, and the like. The driving part 43 includes a pulse motor and the like and moves respective lenses of the variable power lens group 16 in the optical axis direction to change the focal length. The driving part 44 includes a pulse motor and the like and moves the cylindrical lens 17 and the photodetector 18 in the optical axis direction. The driving part 45 includes a pulse motor and the like and moves the entire optical system in a back/forth direction with respect to the eye E. The calculation/processing part 42 forms a sectional image of the eye E based on an output signal from the photodetector 18. The controller 46 has a switch 46a for sending a signal to the driving part 45, a switch 46b for sending a signal to the driving part 43, an image-pickup switch 46c, and the like. The storing part 47 stores the formed sectional image of the eye E.

Incidentally, by changing the focal length of the lens for condensing the light dispersed into the frequency components by the grating mirror at the photo-receiving surface of the photodetector, the ophthalmic OCT apparatus consistent with the preferred embodiment varies a spectral characteristic of the spectrometer part and obtains a sectional image of a large range in the depth direction at low resolution and a sectional image of a narrow range in the depth direction at high resolution. Hereinafter, a principle thereof will be described. It should be noted that Δ denotes the entire photodetector (CCD) and δ denotes one pixel on the photodetector.

Letting f denote the focal length of the lens in the spectrometer part, N denote the number of gratings of the grating mirror (number per millimeter), m denote the order of diffraction, β denote a diffraction angle, and λ denote a wavelength, the following expression 1 holds in respect of coordinate x on the CCD.

$$\delta x = f \cdot \delta \beta = f \frac{\partial \beta}{\partial \lambda} \delta \lambda = f \frac{Nm}{\cos \beta} \delta \lambda \qquad \text{Expression 1}$$

Letting $N_{CCD}$ and $X_{CCD}$ denote the effective number of pixels of the CCD and a width thereon in the dispersing direction of the grating mirror, respectively, and $\Delta \lambda_{CCD}$ denote a wavelength width in dispersing onto the CCD, the following expression 2 holds.

$$\Delta\lambda_{CCD} = \frac{\delta\lambda}{\delta\chi} X_{CCD} = \frac{\cos\beta}{fNm} X_{CCD} \qquad \text{Expression 2}$$

A scale of a signal, which is obtained by performing discrete Fourier transform or inverse discrete Fourier transform on an interference image on the CCD, can be derived as given by the following expression 3. Here, ω denotes an angular frequency and c denotes the velocity of light.

$$\Delta\omega_{CCD} = \frac{2\pi c}{\lambda^2}\Delta\lambda_{CCD} = \frac{2\pi c}{\lambda^2}\frac{\delta\lambda}{\delta X}X_{CCD} = \frac{2\pi c}{\lambda^2}\frac{\cos\beta}{fNm}X_{CCD} \qquad \text{Expression 3}$$

On that account, one pixel after performing discrete Fourier transform or inverse discrete Fourier transform is given by the following expression 4.

$$\delta t = \frac{1}{\Delta f_{CCD}} = \frac{2\pi}{\Delta\omega_{CCD}} = \frac{\lambda^2}{c \cdot \Delta\lambda_{CCD}} = \frac{\lambda^2}{cX_{CCD}}\frac{fNm}{\cos\beta} \qquad \text{Expression 4}$$

This is equivalent to the following expression 5.

$$\delta z = \frac{c\delta t}{2} = \frac{c}{2\Delta f_{CCD}} = \frac{\pi c}{\Delta\omega_{CCD}} = \frac{\lambda^2}{2\Delta\lambda_{CCD}} = \frac{\lambda^2}{2X_{CCD}}\frac{fNm}{\cos\beta} \qquad \text{Expression 5}$$

In addition, according to the property of discrete Fourier transform, the maximum depth can be expressed by $N_{CCD}/2$; accordingly, an information acquisition range $Z_{max}$ in the depth direction is given by the following expression 6.

$$Z_{max} = \frac{N_{CCD}}{2}\delta z = \frac{N_{CCD}}{2}\frac{\lambda^2}{2\Delta\lambda_{CCD}} = \frac{\lambda^2}{4}\frac{N_{CCD}}{X_{CCD}}\frac{fNm}{\cos\beta} \qquad \text{Expression 6}$$

That is to say, the information acquisition range in the depth direction is proportional to the focal length f of the lens and indirectly proportional to the diffraction angle β. Therefore, if the focal length f of the lens in the spectrometer part is increased, the information acquisition range in the depth direction is enlarged while the resolution is decreased, and if the focal length f is decreased, the resolution is increased while the information acquisition range in the depth direction is narrowed.

Hereinafter, an operation of the apparatus with the aforementioned configuration will be described.

While observing the front image of the anterior segment of the eye E illuminated by the light source 22 which is displayed on the monitor 41, an examiner moves the apparatus in up/down, left/right and back/forth directions using operating means such as a joystick not illustrated and aligns the apparatus to have a predetermined positional relationship with the eye E. Incidentally, in the preferred embodiment, the alignment is performed so that the image-pickup surface of the image-pickup element 21 and the pupil of the eye E have a conjugate positional relationship. When the apparatus is brought to have the predetermined positional relationship with the eye E, the examiner operates the switch 46c to display the sectional image of the anterior segment of the eye E on the monitor 41. Then, the examiner operates the switch 46b to perform switching between the focal lengths of the variable power lens group 16 as appropriate so that a desired sectional image of the anterior segment of the eye E is displayed on the monitor 41.

In other words, the switch 46c being pressed, the control part 40 controls to emit the light from the light source 1 and rotate the galvano mirror 4 to scan the light with respect to the eye E. The reflection light brought by the light which is made to converge in the vicinity of the corneal vertex of the eye E by the object-light projecting optical system 100 (i.e., the object light) and the reflection light brought by the light which is made to converge at the reflection surface of the reference mirror 11 by the reference-light projecting optical system 200 (i.e., the reference light) are synthesized by the half mirror 3 to be interference light. Then, the interference light passes through the condenser lens 13 and the expander lens 14 and enters the grating mirror 15 to be dispersed into the frequency components. The dispersed light passes through the variable power lens group 16 and the cylindrical lens 17 to converge at the photo-receiving surface of the photodetector 18.

The photodetector 18 photo-receives the light dispersed into the frequency components and outputs interference strength for each frequency component as a signal. The calculation/processing part 42 monitors the output signal (interference strength) from the photodetector 18. Incidentally, the light photo-received on the photodetector 18 includes not only the reflection light from an anterior surface of the cornea (i.e., the object light) but also reflection light from a posterior surface of the cornea, anterior/posterior surfaces of a crystalline lens, and the like (i.e., the object light). Accordingly, interference light of this reflection light (i.e., the object light) and the reference light is photo-received on the photodetector 18 as a function of frequency.

The calculation/processing part 42 performs Fourier transform to analyze the output signal from the photodetector 18 at the time when the interference strength is maximized. Since the interference light includes the reflection light from respective phase objects of the eye E (e.g., the anterior/posterior surfaces of the cornea, the anterior/posterior surfaces of the crystalline lens, and the like) (i.e., the object light), Fourier transform on the output signal from the photodetector 18 enables obtaining depth information on the respective phase objects such as the cornea and the crystalline lens of the eye E. The calculation/processing part 42 forms a sectional image of the anterior segment of the eye E based on the obtained depth information, and the control part 40 controls the monitor 41 to display the formed sectional image of the anterior segment of the eye E.

Figure 3:
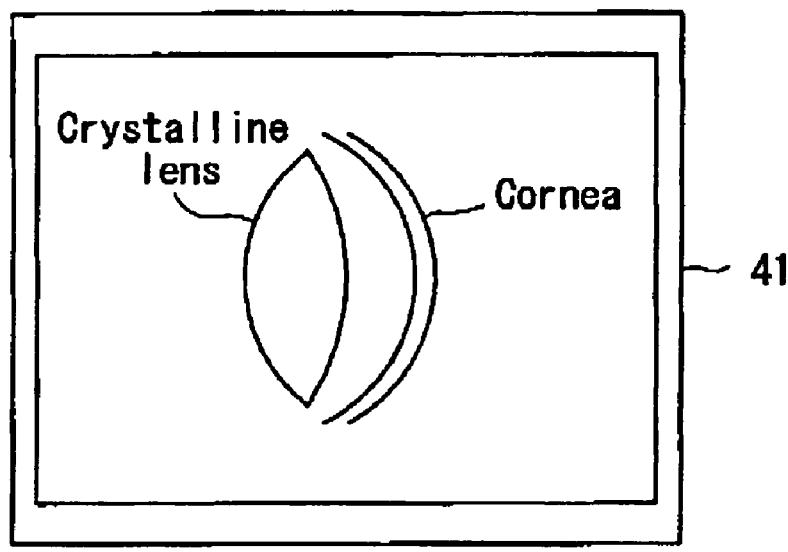
FIGS. 3A and 3B are views showing a difference between sectional images obtained by varying a spectral characteristic.
Figure 3:
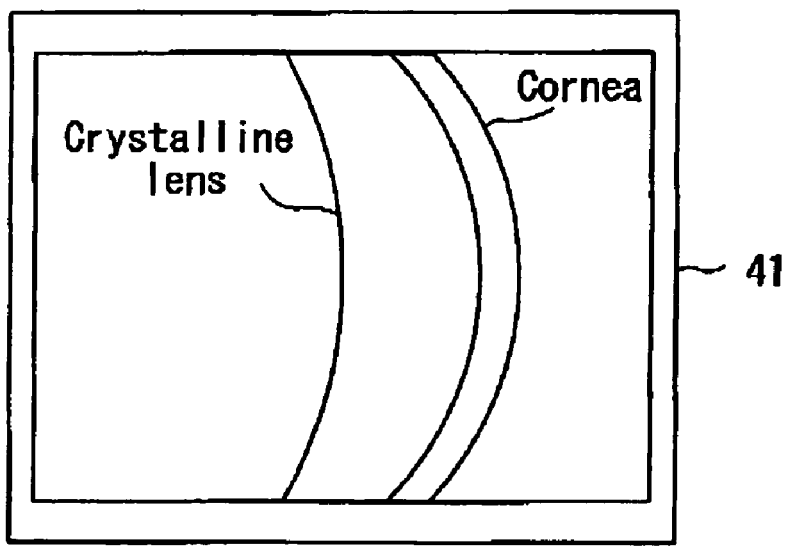

When the focal length of the variable power lens group 16 is long, the sectional image of the entire anterior segment of the eye E can be displayed on the monitor 41 as shown in FIG. 3A since the information acquisition range in the depth direction can be enlarged. Then, the examiner operates the switch 46a to gradually move the entire optical system in the back/forth direction with respect to the eye E so as to position a portion desired to magnify at the center of a screen of the monitor 41. If the switch 46b is operated in this state, the control part 40 controls the driving part 43 to move the respective lenses of the variable power lens group 16 in the optical axis direction so as to decrease the focal length. At this time, the variable power lens group 16 is moved to decrease the focal length while retaining the grating mirror 15 at the anterior focal point of the variable power lens group 16. In addition, according to the decrease in the focal length of the variable power lens group 16, the control part 40 controls the driving part 44 to move the cylindrical lens 17 and the photodetector 18 in the optical axis direction so as to position the photo-receiving surface of the photodetector 18 at the posterior focal point of the variable power lens group 16. When the focal length of the variable power lens group 16 becomes short, a frequency range in the spectrometer part becomes wider than that in the case of the long focal length; accordingly, the sectional image of the portion desired to magnify can be obtained at high resolution as shown in FIG. 3B.

In short, in the ophthalmic OCT apparatus consistent with the preferred embodiment, by increasing the focal length of the variable power lens group 16 to narrow the frequency range of the spectrometer part, a sectional image of a larger depth-direction range can be obtained as compared to a conventional ophthalmic OCT apparatus based on spectral interference. In addition, by decreasing the focal length of the variable power lens group 16 to widen the frequency range of the spectrometer part, a sectional image of a desired portion can be obtained at high resolution.

Incidentally, though the variable power lens group 16 is switched between two focal lengths in the preferred embodiment, the present invention is not limited thereto and may be switched between three or more focal lengths.

In addition, though the spectral characteristic of the spectrometer part is varied by changing the focal length of the variable power lens group 16 in the preferred embodiment, the present invention is not limited thereto and may be varied by an other method. For example, as given by the above expression 6, the information acquisition range $Z_{max}$ in the depth direction is changed not only by the focal length f of the lens but also by the diffraction angle $\beta$ of the grating mirror. Therefore, it is essential only that an arrangement angle of the grating mirror 15 is changed so as to decrease $\cos \beta$ in a case where the information acquisition range is to be enlarged, and the arrangement angle of the grating mirror 15 is changed so as to increase $\cos \beta$ in a case where a sectional image at high resolution is to be obtained even if the information acquisition range is narrowed. Besides, it is essential only that arrangement positions of the condenser lens, the photodetector and the like are accordingly changed in a case where the arrangement angle of the grating mirror 15 is changed.

In addition, though the information acquisition range in the depth direction is enlarged by the aforementioned mechanism in the preferred embodiment, the present invention is not limited thereto. A sectional image in a large depth-direction range can be obtained at high resolution by, for example, sequentially obtaining sectional images of a narrow depth-direction range at high resolution while the apparatus is moved with respect to the eye E and combining the obtained sectional images through image processing.

In addition, though the light to be the object light is made to converge in the vicinity of the corneal vertex of the eye E in the preferred embodiment, the present invention is not limited thereto. It is essential only that the reflection light from the phase objects of the eye (the cornea, the crystalline lens, and the like) be dispersed into the frequency components and photo-received on the photodetector. For example, the light to be the object light may be made to converge in the vicinity of the pupil of the eye.

Further, though the grating mirror (diffraction grid) is used as the dispersing means for dispersing the synthetic light of the object light and the reference light into the frequency components in the preferred embodiment, the present invention is not limited thereto. Some other dispersing means such as a prism and an acoustic optical element can be employed.

In addition, though the ophthalmic OCT apparatus consistent with the preferred embodiment is the apparatus for picking up the sectional image of the anterior segment of the eye, the present invention is not limited thereto and may be applied to, for example, an apparatus for measuring a surface shape, a depth dimension such as an axial length, and the like of the eye.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An apparatus for obtaining depth information on an object of measurement using optical coherence tomography based on spectral interference, the apparatus comprising:

an interference optical system arranged to split a light with a short coherence length in order to use a part of the light as a measurement light of a measurement light projecting optical system and another part of the light as a reference light of a reference optical system, to make the measurement light converge at respective measurement points of the object by using an objective lens, and to synthesize the measurement light reflected from the object and the reference light to be an interference light; and a spectrometer unit including:
a dispersing element arranged to disperse the interference light into frequency components;
an array of light receiving elements arranged to photo-receive a dispersed light, the array of light receiving elements being disposed in a position conjugate with the object; and
means arranged to vary a spectral characteristic of a light to be photo-received by changing a frequency range stepwise or continuously, wherein
the spectral characteristic varying means comprises a variable power optical system disposed between the dispersing element and the array of light receiving elements.

2. The apparatus according to claim 1, wherein the measurement light projecting optical system includes a scanning unit which scans the measurement light in at least one direction.

3. The apparatus according to claim 1, wherein the object comprises an anterior segment of an eye.

* * * * *